United States Patent [19]

Herlyn

[11] Patent Number: 5,130,127
[45] Date of Patent: Jul. 14, 1992

[54] HUMAN TUMOR THERAPY USING BETA (1-3) GLUCANLENTINAN AND ANTI-TUMOR ANTIBODIES

[75] Inventor: Dorothee Herlyn, Wynnewood, Pa.

[73] Assignee: The Wistar Institute, Philadelphia, Pa.

[21] Appl. No.: 707,281

[22] Filed: May 28, 1991

Related U.S. Application Data

[63] Continuation of Ser. No. 710,233, Mar. 11, 1985, abandoned.

[51] Int. Cl.$^5$ ............................................. A61K 39/00
[52] U.S. Cl. .................................................. 424/85.8
[58] Field of Search ........................... 424/858; 514/54

[56] References Cited

PUBLICATIONS

Herlyn et al. PNAS 79 1982.
Chihara et al. Rev of Immunol & Immuno phar. 1982.
Maed et al.-Gann 64 1973.
Ball et al., Blood, vol. 62, No. 6, 1983, pp. 1203-1210.
Dillman et al., Blood, vol. 59, No. 5, 1982, pp. 1036-1045.
Foon et al., Blood, vol. 64, No. 5, 1984, pp. 1085-1093.
Miller et al., Blood, vol. 58, No. 1, 1981, pp. 78-86.
Miller et al., The Lancet, vol. II, No. 8240, pp. 226-230.
Miller et al., The New Eng. J. Med., vol. 306, No. 9, pp. 517-522.
Nadler et al., Cancer Research, vol. 40, No. 9, pp. 3147-3154.
Ritz et al., Blood, vol. 58, No. 1, 1981, pp. 141-152.
Bell, Journal of Supramolecular Structure, vol. 8, 1979, p. 281, Abstract No. 728. "Monclonal v. Polyclonal Stimulation by B-1355 Polyglucan".
Herlyn, International Journal of Immunopharmacology, vol. 7, 1985, p. 332, Abtract No. 21, "Stimulation of Monoclonal Antibody-Dependent Macrophage-Mediated Cytotoxicity Against Human Tumors by Lentinan".
Herlyn, Biological Abstracts, vol. 80, No. 7, 1985, Abstract No. 60486, "Monoclonal Antibody-Dependent Murine Macrophage-Mediated Cytotoxicity Against Human Tumors is Stimulated by Lentinan".
Herlyn, Japanese Journal of Cancer Research (GANN), vol. 76, pp. 37-42, 1985, "Monoclonal Antibody-Dependent Murine Macrophage-Mediated Cytotoxicity Against Human Tumors is Stimulated by Lentinan".
Dennert et al, "Brief Communication: Antitumor Polysaccharide Lentinan—At Cell Adjuvant," J. Natl. Cancer Institute, vol. 51, No. 5, 1727-1729 (1973).
Maeda et al, "Periodical Consideration on the Establishment of Antitumor Action in Host and Activation of Peritoneal Exudate Cells by Lentinan," Gann, 64, 351-357 (1973).
Herlyn et al, "Inhibition of Growth of Colorectal Carcinoma in Nude Mice by Monoclonal Antibody," Cancer Research 40, 717-721 (1980).
Hamuro et al, "Induction of Cytotoxic Peritoneal Exudate Cells by T-Cell Immune Adjuvants of the $\beta(1\rightarrow3)$ Glucan-Type Lentinan and Its Analogues," Immunology, vol. 39, No. 1, 551-559 (1980).
Herlyn et al, "IgG2a Monoclonal Antibodies Inhibit Human Tumor Growth Through Interaction with Effector Cells," Proc. Natl. Acad. Sci. U.S.A. vol. 79, 4761-4765 (1982).
Chihara et al, "Lentinan: Biological Activities and Possible Clinical Use," National Cancer Center Research Institute, Tsukiji, Tokyo and Research Institute for Microbial Diseases, Osaka University, Suita, Osaka, Japan (Estratto dalla rivista EOS No. 3, vol. 11 (1982).
Steplewski et al, "Human Macroph ages Armed with Murine Immunoglobulin G2a Antibodies to Tumors Destroy Human Cancer Cells," Science vol. 211, 865-867 (1983).
Sears et al, "Effects of Monoclonal Antibody Immunotherapy on Patients with Gastrointestinal Adenocarcinoma", J. Biological Response Modifiers, vol. 3, No. 2, 138-150 (1984).

Primary Examiner—Garnette D. Draper
Attorney, Agent, or Firm—Banner, Birch, McKie & Beckett

[57] ABSTRACT

A therapeutic method for treating human tumors in vivo is provided wherein lentinan is administered to the patient followed by treatment with anti-tumor monoclonal antibodies.

18 Claims, 2 Drawing Sheets

HUMAN TUMOR THERAPY USING BETA (1-3) GLUCANLENTINAN AND ANTI-TUMOR ANTIBODIES

The invention described herein was made in the course of work under a grant or award from the Department of Health, Education and Welfare.

This is a continuation of copending application Ser. No. 07/710,233 filed on Mar. 11, 1985, now abandoned.

TECHNICAL FIELD

The present invention is directed to a therapeutic method for treating human tumors. More specifically, the present invention is directed to a method of treating human tumors with monoclonal antibodiies in combination with lentinan.

BACKGROUND OF THE INVENTION

In previous studies it has been shown that murine monoclonal antibodies (MAb) of IgG2a isotype that bind to human tumor cells specifically inhibit growth of the tumor cells in nude mice. Recently, a Mab of IgG3 isotype has also been shown to be effective. Herlyn et al., (1980) *Cancer Res.* 40:71 7-721; Herlyn & Koprowski, (1982) *Proc. Nato. Acad. Sci. U.S.A.* 79:4761-4765. There was evidence suggesting that tumor growth inhibition by the MAb probably was mediated by macrophages since treatment of nude mice with silica abolished the tumoricidal effects of the MAb. Furthermore, antibody-dependent macrophage-mediated cytotoxicity (ADMC) assays with human tumor cells in cultyre resulted in specific lysis of these cells. Thioglycollate-elicited murine peritoneal macrophages were used in these assays. Human macrophages have also been shown to lyse tumor targets coated with MAb. Steplewski et al., (1983) *Science* 211:865-867. Macrophages, therefore, are strongly implicated as the effector cells mediating immunotherapeutic effects of, for example, MAb administered to gastrointestinal cancer patients. See. e.g., Koprowski in *Proceedings of the IV Armand Hammer Cancer Synposium*, pp. 17-38 (Boxx, Langman, Trowbridge & Dulbecco eds. 1984); Sears et al., (1984) *J. Biol. Response Mod.* 3:138-150.

SUMMARY OF THE INVENTION

It is an object of the present invention to provide a method of tumor therapy.

Another object of the present invention is to provide a method of tumor therapy employing MAbs in which the therapeutic effects of the MAbs are enhanced.

Yet another object of the present invention is to provide a method of tumor therapy in which the therapeutic effect of MAbs is enhanced by the stimulation of macrophages.

These and other objects of the present invention are achieved by a therapeutic method for human tumors comprising:

administering to a tumor-bearing patient β-(1-3) glucan lentinan in an amount sufficient to stimulate macrophage activity; and administering to said patient anti-tumor monoclonal antibodies after said lentinan administration, said monoclonal antibodies having an isotype selected from the group consisting of IgG2a and IgG3, and binding an antigen on the surface of said patient's tumor cells.

DETAILED DESCRIPTION OF THE INVENTION

Figure 2:
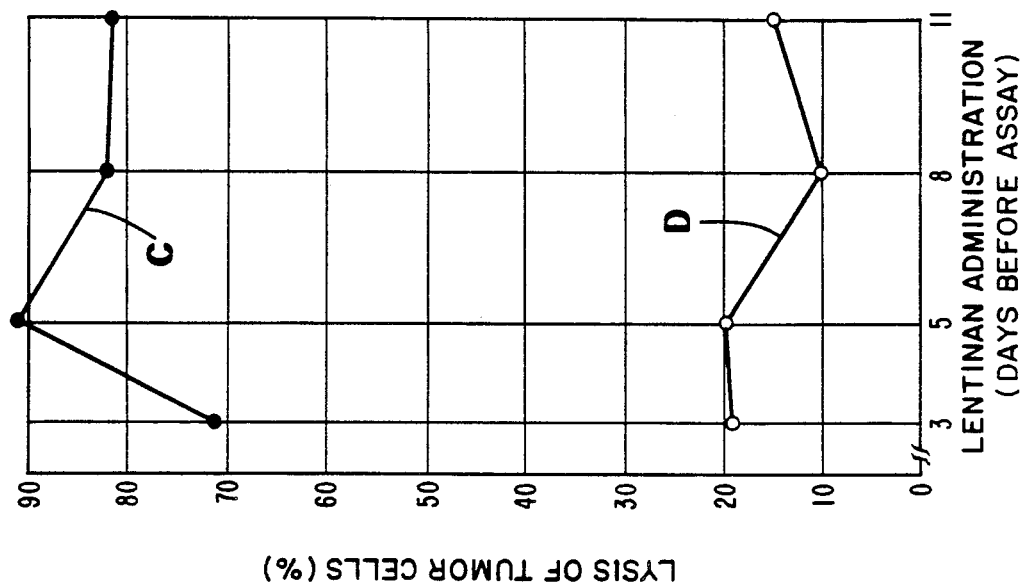
FIG. 2 shows the kinetics of macrophage stimulation by lentinan. Macrophages were collected at various times after administration of lentinan to mice and assayed for ADMC reactivity with SW1116 target cells in the presence of anti-colon carcinoma MAb(o) (curve C). Minimal lysis was obtained in the presence of control anti-influenza virus MAb (o) (curve D).

It has been discovered that the stimulation of macrophages in vivo with β(1-3) glucan lentinan (hereinafter lentinan) renders them cytotoxic against tumor cells in vitro, in the presence of anti-tumor monoclonal antibodies of particular isotypes (Table 1).

Generally, the therapeutic method of the present invention comprises first administering lentinant to a tumor-bearing patient to stimulate macrophages, and the administering anti-tumor MAbs to the patient. Lentinan is a neutral polysaccharide whose physical and chemical properties are fully characterized. Briefly, it is isolated from a hot water extract from the fruit body of *Lentinus edodes* (Berk.) Sing. The chemical structure of lentinan is reported to be a β-1,3-glucan, with an average moleculare weight distributed in the range between $4 \times 10^5$ and $8 \times 10^5$ daltons by gel permeation chromatography. According to elementary analysis, the molecular formula of lentinan is $(C_6H_{10}O_5)$. See generally, Chihara & Taguchi, (1982) *Rev. Immunol. Immunopharmacol (Rome)* 2:92-104.

The use of lentinan as a macrophage potentiator has been found to be preferred to other possible potentiators because it is a relatively safe compound to administer to patients. Furthermore, it is more effective than thioglycollate. Other agents, such as BCG and C . parvum, do not activate macrophages for tumor cell lysis by IgG2a MAbs.

The effectiveness of the therapeutic regimen of the present invention is dependent upon the timing and dosages of lentinan to the patient. Animal studies indicate that there is an optimal dose of lentinan with higher doses resulting in a decrease in macrophage activation. Other animal studies have indicated that the timing of lentinan administration is an important factor bearing upon the effectiveness of the therapy. Generally, optimal macrophage activation was observed from about 3 to about 5 days following the administration of lentinant. These time periods are based upon results of animal studies and may be varied somewhat as additional clinical data on humans is available. One skilled in the art, however, being aware that there is an optimal dosage and that there are timing effects in animal studies will be able to establish an optimal dosage and timing of lentinant administration of human patients through routine clinical trials.

After a macrophage-stimulating quantity of lentinan has been administered to a patient, anti-tumor MAbs are administered to the patient; i.e., antibodies that bind an antigen on the surface of the patient's tumor cells. Desireably, the antibodies are administered at about the time that macrophage activation reaches a maximum, that is about 3 to about 5 days after lentinan activation. The MAbs should be of isotype IgG2a or IgG3, and preferably of isotype IgG2a. Macrophages stimulated by lentinan were not found to be cytotoxic for tumor cells coated with MAbs of isotype IgG2b, IgM, or IgA. Preferably, the MAbs are human MAbs.

The preparation of MAbs from immortal cell lines are well known in the art. For example, immortal, antibody-producing cell lines can be produced from normal B cells by hybridoma technology, Epstein-Barr virus transformation, or transformation with oncgenic DNA. See. e.g., M. Schreier et al., *Hybridoma Techniques* (Cold Spring Harbor Laboratory 1980); Hammerling et al., *Monoclonal Antibodies and T-Cell Hybridomas* (Elsevier Biomedical Press 1981); Kennett, et al., *Monoclonal Antibodies* (Plenum Press 1980); Kozbor et al., (19822) *Proc. Natl. Acad. Sci. U.S.A.* 79:6651-6655; Jonak et al., (1983) *Hybridoma* 2:124; *Monoclonal Antibodies and Functional Cell Lines* (Kennett, Becktol & McKearn eds. 1983); Kozbor et al., (1983) *Immunology Today* 4:72-79. The type of immortal cell line from which the MAbs are produced is not critical.

Those that are skilled in the art are familiar with the use of MAbs in tumor therapy and the establishment of optimal dosages through routine clinical trials is well within the skill of the art. See e.g. Sears et al., *J. Biol. Response Mod* ., 3:138-150 (1984). The examples below in mouse models will aid those skilled in the art in establishing optimum effective dosages and in timing dosages for both lentinan and anti-tumor MAbs in the treatment of human patients.

Although applicants do not wish to be bound by this theory, it is believed that lentinan indirectly enhances anti-tumor cytotoxic effects of macrophages by direct activation of the alternated pathway of the complement system and/or by stimulating helper T-cells. The possible T-cell dependency is supported by the failure to find enhancing effects in athymic mice implanted with human tumors and treated with MAb.

The following examples are presented for illustrative purposes only and are not intended to limit the scope of the present invention.

MATERIALS AND METHODS

Human Tumor Cell Lines

Melanoma cell line WM-9, colorectal carcinoma cell line SW1116 and pancreatic carcinoma cell line Capan have been described. See Herlyn et al., (1983) *Cancer Invest.* 1:215-224; Koprowski et al., (1979) *Somat. Cell. Genet.* 5:957-971; Steplewski. et al., (1979) *Eur. J. Immunol.* 9:94-96.

Murine MAbs

The MAbs included in this study are listed in Table I. They were produced against colorectal carcinomas, melanomas and pancreatic carcinomas and have been described in detail previously. See Hansson et al., (1983); *J. Biol. Chem.* 258:4090-4097; Herlyn et al., (1983) supra; Koprowski et al., (1979), supra.

Murine Macrophages

Preparation of thioglycolate-elicited CBA macrophages adherent to wells of microtiter plates has been described. Lentinan-activated macrophages were obtained from 6- to 10-week-old CBA mice by intraperitoneal (i.p.) injection of 2.5 mg/kg body weight (BW) of lentinan (Ajinomoto Co., Tokyo, Japan) unless otherwise stated. Macrophages were collected at various times thereafter and plated as described for thioglycollate-elicted macrophages. See Herlyn andd Koprowski (1982) *Proc. Natl. Acad. Sci. U.S.A.* 79:4761-4765. Thioglycollate and lentinan-stimulated adherent peritoneal cells consisted of 94% and 85% (mean of 3 experiments) macrophages, respectively, as determined by latex phagocytosis and non-specific esterase staining. Boltz-Nitulescu & Foerster, (1979) *Immunology* 38:621-630; Tucker et al. (1977) Journal of Immunological Methods 14:267-269. The cells contaminating the macrophages morphologically resembled fibroblasts and were non-phagocytic and esterase-negative.

ADMC Assays

The ADMC assay with [methyl-$^3$H]thymidine-labeled target cells was performed as described. See Herlyn & Koprowski (1982), supra. All ADMC values given are corrected for percent lysis obtained in the presence of anti-influenza virus control MAb.

Binding Assays

Binding of iodinated MAbs to Fc receptors on thioglycollate- or lentinan-activated macrophages was determined by adding to the adherent macrophages either various amount of [$^{125}$I] MAb or constant amounts of [$^{125}$I] MAb mixed with increasing amounts of unlabeled MAb as described. Unkeless et al., (1975) J. Exp. Med. 142:1520-1533. Association constants of MAb binding and maximal number of binding sites per macrophage were determined by the method of Scatchard.

Statistical Analysis

Data were analyzed using the Student's t-test. A probability of less than 5% (p less than 0.05) was considered significant.

RESULTS

Effect of Various Lentinan Dosages on ADMC by MAb 17-1A

Figure 1:
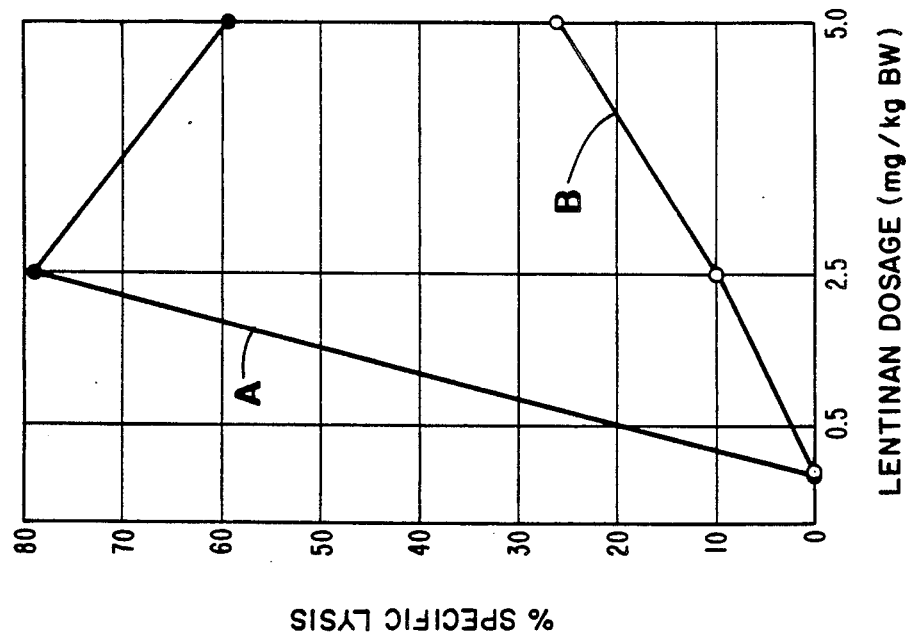
FIG. 1 shows the effect of various lentinan dosages on ADMC reactivity of murine peritoneal macrophages against carcinoma SW1116 target cells, in the presence of IgG2a anti-colon carcinoma MAb. Curve A is at an effector to target cell ratio of 50; curve B is at an effector to target ratio of 10.

Between 0.25 and 5 mg lentinan per kg were administered to mice i.p.; ADMC reactivity of peritoneal macrophages against colorectal carbinoma cells SW-1116 coated with MAb 17-1A was assayed 3 days later at two different effector-to-target (E:T) cell ratios. As can be seen from FIG. 1, the ADMC levels were highest when lentinan was used at 2.5 mg/kg BW, and E:T cell ratio was 50. Whereas ADMC values increased over the entire dosage range at the lower E:T cell ratio of 10, these values were significantly (p less than 0.05) lower than those obtained at an E:T cell ratio of 50. Therefore, in the ADMC assays described below, macrophages were stimulated by injection of 2.5 mg lentinan per kg BW and E:T cell ratios of 50 were used. Increasing the E:T cell ratios above 50 did not result in higher ADMC values. Non-stimulated (resident) macrophages caused only 20% and 0% lysis in the present of MAb 17-1A at E:T cell ratios of 50 and 10, respectively.

Kinetics of Macrophage Stimulation by Lentinan

Peritoneal macrophages were assayed for ADMC reactivity, 3, 5, 8 and 11 days following i.p. injection of 2.5 mg lentinan per kg BW. As can be seen from FIG. 2, ADMC activity of macrophages in the presence of specific MAb was highest 5 days following injection of lentinan, where as values obtained in presence of control MAb did not differ on the various days tested. The increase in the percentage of non-phagocytic cells in the macrophage preparations from day 5 after the injection of lentinan might account for the decrease in macrophage activity with time. Therefore, macrophages were generally collected 3–5 days following the injection of lentinan.

Comparison of Lentinan and Thioglycollate-Stimulated Macrophages in ADMC

Figure 3:
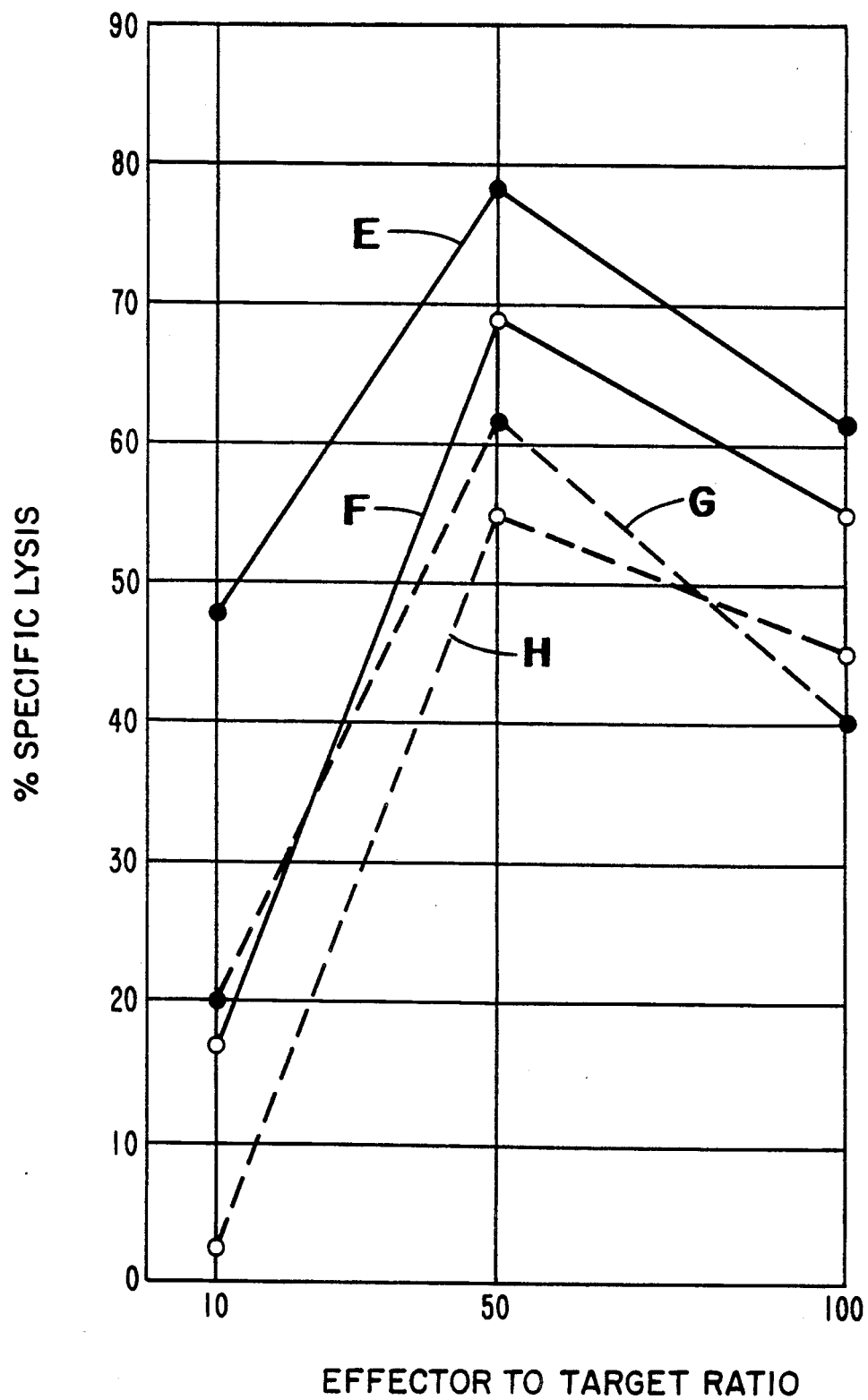
FIG. 3 presents a comparison of the ADMC reactivity of lentinan-stimulated macrophages (solid lines on Figure) to thioglycollate-stimulated macrophages (dashed lines on Figure) in lysing melanoma target cells (o), or colon carcinoma cells (•), in the presence of specific MAbs.

ADMC reactivity of lentinan-stimulated macrophages was compared with the reactivity of thioglycollate-elicited macrophages which have been used by us previously to demonstrate ADMC-reactivity of IgG2A MAbs. See Herlyn & Koprowski (1982), supra. Lentinan-activated macrophages shown higher lytic activities against colon carcinomas or melanomas coated wtih IgG2a MAbs as compared to thioglycollate-elicited macrophages (FIG. 3). These differences were significant (p less than 0.05) at all E:T cell ratios tested.

Comparison of MAbs of Various Isotypes in ADMC Assays with Lentinan-Stimulated Macrophages ADMC-reactivities of MAbs produced against various human tumors and representing 6 different isotypes are presented in Table I. Lentinan-activated macrophages were used as effector cells. In these assays, all the IgG2a and IgG3 MAbs and some of the IgG1 MAbs were reactive whereas IgG2b, IgA and IgM MAbs were non-reactive.

TABLE 1
MAbs of Various Isotypes in ADMC with Lentinan-Stimulated Macrophases

| MAB Isotype | MAB Code | Target Origin[1] | Target Code | % Specific lysis[2] Lentinan-macrophages |
|---|---|---|---|---|
| IgG1 | ME8211 | MEL | WM-9 | 0 |
|  | ME7771 | MEL | WM-9 | 0 |
|  | ME529 | MEL | WM-9 | 12.5 |
|  | 19-9 | CRC | SW1116 | 60.2 |
| IgG2a | 17-1A | CRC | SW1116 | 79.4 |
|  | ME377 | MEL | WM-9 | 69.8 |
|  | ME5073 | MEL | WM-9 | 42.4 |
|  | ME121 | MEL | WM-9 | 24.6 |
| IgG2b | ME3174 | MEL | WM-9 | 0 |
|  | ME7965 | MEL | WM-9 | 0 |
| IgG3 | PC2111 | PC | Capan | 34.0 |
|  | PC2195 | PC | Capan | 15.4 |
| IgM | 38a | CRC | SW1116 | 0 |
|  | ME919 | MEL | WM-9 | 0 |
| IgA | PC8352 | PC | Capan | 0 |

[1] Abbreviations: CRC = colorectal carcinoma, MEL = melanoma, PC = pancreatic carcinoma.
[2] Values represent means of triplicate determinations in two independently performed experiments. E:T cell ratios were 50. All values differed significantly (p ≦ 0.05) from control values obtained with anti-influenza virus MAb. Values that did not differ from controls were designated zero.

Scatchard Analysis of Mab Binding to Murine Macrophages

Lentinan- and thioglycollate-stimulated macrophages bound 2.8 and $3.8 \times 10^4$ molecules of MAb 17-1A per macrophage, respectively. These values did not differ significantly (p less than 0.05). The association constants were $0.2 \times 10^8$ mole $^{-1}$ for both types of macrophages.

Since variations will be apparent to those skilled in the art, it is intended that this invention be limited only by the scope of the appended claims.

I claim:

1. A method of enhancing the therapeutic effect of anti-tumor antibodies, comprring:
   administering to a tumor-bearing patient beta(1-3) glucan lentinan in an amount sufficient to stimulate macrophage activity; and
   administering to said patient an anti-tumor monoclonal antibody after said lentinan administration, said monoclonal antibody having an isotype selected from the group consisting of IgG2a and IgG3, said monoclonal antibody binding an antigen on the surface of said patient's tumor cells and inhibiting growth of said tumor cells upon administration to said patient.

2. The method of claim 1 wherein said anti-tumor monoclonal antibodies are monoclonal antibodies directed against human antigens.

3. The method of claim 1 wherein said monoclonal antibodies are of the isotype IgG2a.

4. The method of claim 2 wherein said monoclonal antibodies are of the isotype IgG2a.

5. The method of claim 1 wherein said administration of lentinan occurs about 3 to 5 days prior to said monoclonal antibody administration.

6. The method of claim 2 wherein said administration of lentinan occurs about 3 to 5 days prior to said monoclonal antibody administration.

7. The method of claim 3 wherein said administration of lentinan occurs about 3 to 5 days prior to said monoclonal antibody administration.

8. The method of claim 4 wherein said administration of lentinan occurs about 3 to 5 days prior to said monoclonal antibody administration.

9. A therapeutic method of treating human carcinomas comprising:
   administering to a carcinoma-bearing patient beta(-1-3) glucan lentinan in an amount sufficient to stimulate macrophage activity; and
   administering to said patient anti-carcinoma monoclonal antibodies after said lentinan administration, said monoclonal antibodies having an isotype selected from the group consisting of IgG2a and IgG3, said monoclonal antibodies binding an antigen on the surface of said patient's carcinoma cells.

10. The method of claim 9 wherein said carcinoma cells are pancreatic carcinoma cells.

11. The method of claim 9 wherein said carcinoma cells are colon carcinoma cells.

12. The method of claim 9 wherein said monoclonal antibodies are of the isotype IgG2a.

13. The method of claim 9 wherein said monoclonal antibodies are of the isotype IgG3.

14. The method of claim 9 wherein said administration of lentinan occurs about 3 to 5 days prior to said monoclonal antibody administration.

15. A therapeutic method of treating human melanomas comprising:
    administering to a melanoma-bearing patient beta(-1-3) glucan lentinan in an amount sufficient to stimulate macrophage activity; and
    administering to said patient anti--melanoma monoclonal antibodies after said lentinan administration, said monoclonal antibodies having an isotype selected from the group consisting of IgG2a and IgG3, said monoclonal antibodies binding an antigen on the surface of said patient's melanoma cells.

16. The method of claim 15 wherein said monoclonal antibodies are of the isotype IgG2a.

17. The method of claim 15 wherein said monoclonal antibodies are of the isotype IgG3.

18. The method of claim 15 wherein said administration of lentinan occurs about 3 to 5 days prior to said monoclonal antibody administration.

* * * * *